US008663575B2

(12) United States Patent
Maurer et al.

(10) Patent No.: US 8,663,575 B2
(45) Date of Patent: Mar. 4, 2014

(54) SAMPLE HOLDER FOR DYNAMIC LIGHT SCATTERING

(75) Inventors: Elisabeth Maurer, Vancouver (CA); Georg Maurer, Vancouver (CA); Keddie Brown, Vancouver (CA); Gyasi Bourne, Vancouver (CA); Kenneth MacCallum, Victoria (CA); Paul Charlebois, Victoria (CA)

(73) Assignee: Canadian Blood Services, Ottawa (CA)

( * ) Notice: Subject to any disclaimer, the term of this patent is extended or adjusted under 35 U.S.C. 154(b) by 795 days.

(21) Appl. No.: 12/807,208

(22) Filed: Aug. 31, 2010

(65) Prior Publication Data

US 2011/0063607 A1    Mar. 17, 2011

Related U.S. Application Data

(63) Continuation-in-part of application No. 11/208,080, filed on Aug. 19, 2005, now Pat. No. 7,842,247.

(51) Int. Cl.
*C12Q 1/68* (2006.01)
*B01L 3/00* (2006.01)
*G01N 31/00* (2006.01)
*C12M 1/34* (2006.01)
*G01N 21/01* (2006.01)

(52) U.S. Cl.
USPC ............. 422/401; 422/50; 422/500; 422/501; 422/502; 422/503; 436/10; 435/287.1; 356/244; 356/336; 356/337; 165/80.3; 165/48.1; 165/61

(58) Field of Classification Search
USPC ............ 422/50, 500–503; 436/10; 435/287.1; 356/244, 336, 337; 165/80.3, 48.1, 61
See application file for complete search history.

(56) References Cited

U.S. PATENT DOCUMENTS

| 4,204,117 | A | * | 5/1980 | Aberle et al. | 250/287 |
|-----------|---|---|--------|--------------|---------|
| 4,739,467 | A | * | 4/1988 | Furusawa | 700/28 |
| 5,092,674 | A | * | 3/1992 | Garner | 356/244 |
| 5,183,042 | A | * | 2/1993 | Harjunmaa et al. | 600/309 |
| 5,324,956 | A | * | 6/1994 | Fagan et al. | 250/573 |
| 5,869,346 | A | * | 2/1999 | Xiaoming et al. | 436/525 |
| 6,094,266 | A | | 7/2000 | Trainer | |
| 6,731,961 | B2 | * | 5/2004 | Braig et al. | 600/310 |
| 7,075,652 | B1 | * | 7/2006 | Sarvazyan et al. | 356/432 |
| 2007/0041877 | A1 | | 2/2007 | Maurer et al. | |

OTHER PUBLICATIONS

International Preliminary Report on Patentability / Written Opinion of the ISR for co-pending PCT Application No. PCT/US2011/049271.

* cited by examiner

*Primary Examiner* — Dean Kwak
(74) *Attorney, Agent, or Firm* — Hancock Hughey LLP

(57) ABSTRACT

There is described a sample holder and associated fluid container assembly for optical analysis of a fluid sample within a translucent container of the fluid container assembly. The sample holder includes clamping members rotatably mounted to a frame for rotation, about parallel axes spaced apart from each other, between a container accepting position in which the clamping members are spaced apart from the translucent container, and an analysis position in the clamping members abut the translucent container. The clamping members each define an optical waveguide slot extending therethrough that is substantially aligned with the translucent container when the clamping members are disposed in the analysis position, to thereby provide optical access to the translucent container for optical analysis of the fluid sample therein.

12 Claims, 13 Drawing Sheets

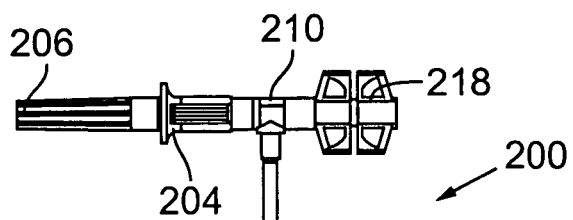
FIG. 6
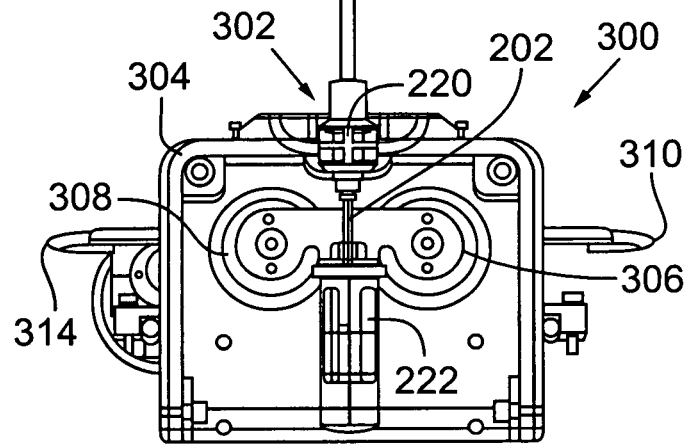
FIG. 7
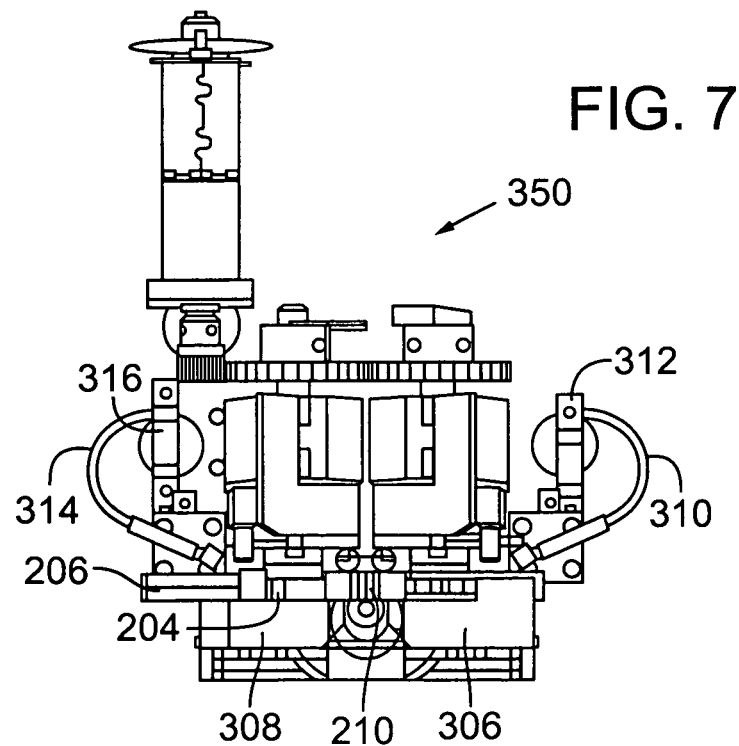

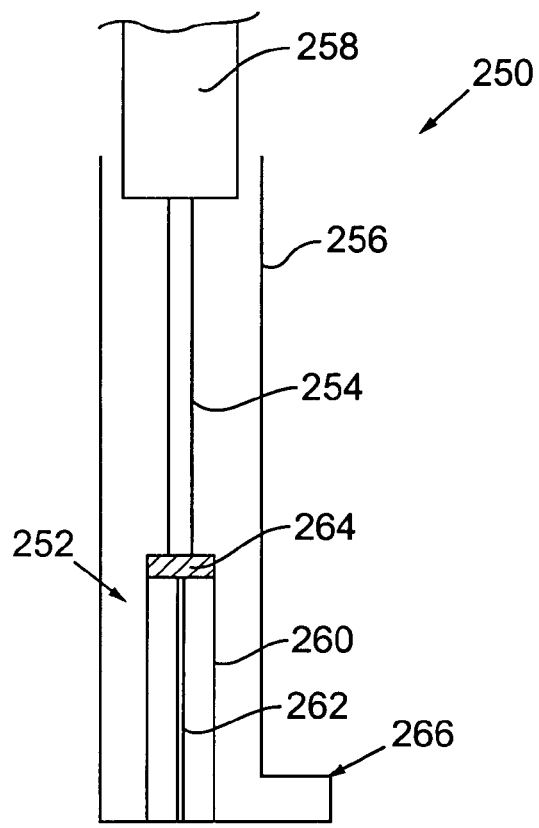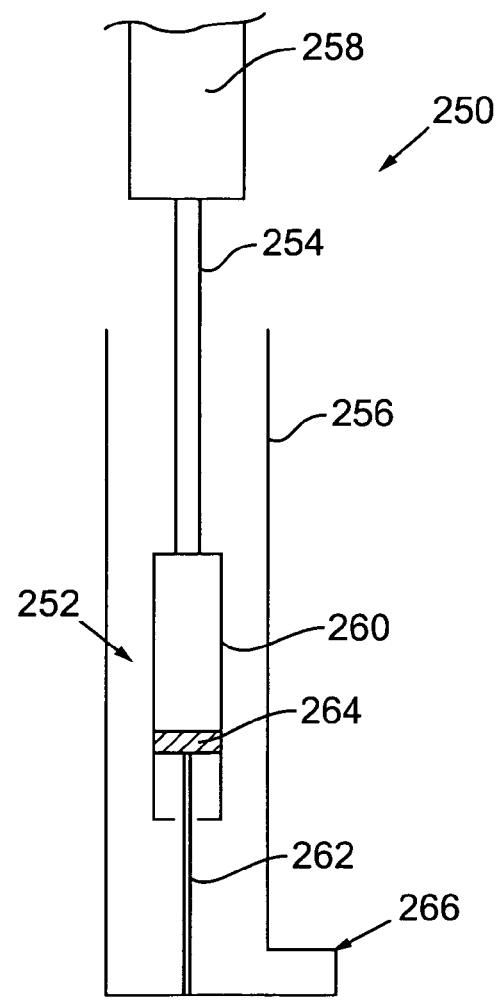
FIG. 9a
FIG. 9b

SAMPLE HOLDER FOR DYNAMIC LIGHT SCATTERING

CROSS-REFERENCE TO RELATED APPLICATIONS

This application is a continuation-in-part of U.S. patent application Ser. No. 11/208,080, filed on Aug. 19, 2005, the entire content of which is incorporated herein by reference.

TECHNICAL FIELD

The present invention relates generally to optical analysis of fluids, colloidal dispersions or suspensions and, in particular, to sample-holding devices for dynamic light scattering (DLS) or quasi-elastic light scattering (QELS).

BACKGROUND

Dynamic light scattering (DLS), which is also known as quasi-elastic light scattering (QELS), is an optical analysis technique that is well known in the art. An optical source such as laser light is focused into the sample. Light scatters when it hits particles suspended in the fluid, such as platelets suspended in solution. The scattered light is collected by light collectors disposed at specific angles relative to the incident light. As is known in the art, the scattered light fluctuates due to Brownian motion of the particles in solution. Using algorithms that are known in the art, these fluctuations of scattered light are then correlated to the particles' mean size and shape which are expressed in terms of hydrodynamic radius.

To perform dynamic light scattering on a fluid sample, the fluid sample is contained within a translucent container (e.g. a capillary or cuvette) that is, in turn, held by a sample holder, also known as a capillary holder or cuvette holder.

A number of sample holders and DLS-type apparatuses having sample-holding compartments are known in the art, for example the Coulter N4 Plus™ from Beckman Coulter, Inc. of Fullerton, Calif. and the DynaPro Titan™ from Wyatt Technology Corporation of Santa Barbara, Calif.

Some sample-holding devices are described in U.S. Patent Application 2005/0094127 (O'Mahony et al.) entitled CUVETTE APPARATUS AND SYSTEM FOR MEASURING OPTICAL PROPERTIES OF A LIQUID SUCH AS BLOOD; U.S. Pat. No. 6,016,193 (Freeman et al.) entitled CUVETTE HOLDER FOR COAGULATION ASSAY TEST; U.S. Pat. No. 6,249,344 (Virag) entitled METHOD AND APPARATUS FOR SEDIMENTATION AND OPTICAL EXAMINATION OF PARTICLES SUSPENDED IN A FLUID, FURTHER A CUVETTE FOR ACCOMPLISHING SAID METHOD; U.S. Design Pat. D442,287 (Pogorzelski) entitled CUVETTE HOLDER; U.S. Design Pat. D271,335 (Simons) entitled CUVETTE HOLDER; U.S. Pat. No. 4,208,127 (Hufenreuter) entitled CUVETTE HOLDER; U.S. Pat. No. 6,488,892 (Burton et al.) entitled SAMPLE-HOLDING DEVICES AND SYSTEMS; U.S. Pat. No. 6,399,026 (Karrai) entitled SAMPLE HOLDER APPARATUS; U.S. Pat. No. 6,266,139 (Mannhardt) entitled CAPILLARY TUBE HOLDER; U.S. Pat. No. 4,278,437 (Haggar) entitled FLUID SPECIMEN HOLDER FOR BIOLOGICAL FLUID TESTING; U.S. Pat. No. 6,239,875 (Verheijen) entitled PHOTOMETRIC MEASURING SYSTEM AND A HOLDER FOR SUCH A SYSTEM; U.S. Pat. No. 6,055,050 (Skiffington) entitled PHOTOMETER AND TEST SAMPLE HOLDER FOR USE THEREIN, METHOD AND SYSTEM; U.S. Patent Application 2004/0233423 (Nakayama et al.) entitled SAMPLE HOLDER FOR SPECTRUM MEASUREMENT AND SPECTROPHOTOMETER; U.S. Pat. No. 5,900,132 (Keenan et al.) entitled CAPILLARY HOLDER; U.S. Pat. No. 5,733,507 (Zakim) entitled BIOLOGICAL CELL SAMPLE HOLDER FOR USE IN INFRARED AND/OR RAMAN SPECTROSCOPY ANALYSIS HOLDER; U.S. Pat. No. 6,188,474 (Dussault et al.) entitled OPTICAL SPECTROSCOPY SAMPLE CELL; U.S. Pat. No. 5,674,457 (Williamson et al.) entitled CAPILLARY MICROCUVETTE; Canadian Patent 1,247,399 (Wyatt et al.) entitled SAMPLE CELL FOR LIGHT SCATTERING MEASUREMENTS; Canadian Patent 1,242,595 (Phillips et al.) entitled SAMPLE CELL FOR LIGHT SCATTERING MEASUREMENTS; and U.S. Pat. No. 5,530,540 (Wyatt et al.) entitled LIGHT SCATTERING MEASUREMENT CELL FOR VERY SMALL VOLUMES.

However, to the extent of Applicant's knowledge, each of these prior-art sample holders is only designed to hold a specific type of container (i.e. either a round capillary or a square cuvette) and furthermore is only designed to only hold a container of a specific size or of a very limited size range. Accordingly, it would be highly desirable to provide a sample holder that redressed this deficiency.

Moreover, many of these prior-art sample holders include means for heating and/or cooling the fluid sample in order to collect DLS measurements at different temperatures. However, these prior-art temperature-controlled sample holders are not designed for efficient and uniform heat transfer because they must provide optical access for both the incident light and the scattered light. In other words, heating or cooling elements are located inefficiently (such as beneath the container) in order to ensure that there is adequate optical access. The prior-art designs have in general failed to optimize both optical access and heat transfer. It would therefore be highly desirable to provide a sample holder that enables efficient and uniform heat transfer without unduly compromising optical access to the sample.

SUMMARY

It is therefore an object of the present invention to provide an improved sample holder.

The sample holder can be integrated into a dynamic light scattering (DLS) system for collecting scattered light from a variety of locations around the sample. Therefore, a DLS system using this sample holder can operate with a single light source, such as a single laser diode, while collecting scattered light by deploying a plurality of light collectors at various locations around the sample holder. This versatile, easy-to-use and efficient sample holder greatly facilitates DLS/QELS or other optical analysis techniques for analyzing platelet solutions, whole blood or other colloids or colloidal dispersions.

In accordance with an aspect of the present invention, there is provided a sample holder for holding a fluid container assembly for optical analysis of a fluid sample within a translucent container of the fluid container assembly, the sample holder comprising: a frame having an opening for receiving at least the translucent container of the fluid container assembly therein; first and second clamping members disposed on opposite sides of the opening, the first and second clamping members being rotatably mounted to the frame for rotation about parallel axes spaced apart from each other, the first and second clamping members being rotatable between a container accepting position in which the first and second clamping members are spaced apart from the translucent container within the opening, and an analysis position in which at least one of the first and second clamping members abuts the translucent container within the opening; and wherein the first and second clamping members each defining at least one optical waveguide slot extending therethrough, the optical waveguide slots being substantially aligned with the translucent container when the first and second clamping members are disposed in the analysis position, to thereby provide optical access to the translucent container for optical analysis of the fluid sample therein.

In accordance with a further aspect, there is provided a sample holder for holding a fluid container assembly for optical analysis of a fluid sample contained within the fluid container assembly, the fluid container assembly having a translucent container enclosed within a movable protective casing, the sample holder comprising: a frame having an opening for receiving the fluid container assembly therein; and first and second clamping members disposed on opposite sides of the opening and each movable between a container accepting position in which the first and second clamping members are spaced apart from the fluid container assembly within the opening, and an analysis position in which at least one of the first and second clamping members abuts the movable protective casing to maintain at least a portion of the translucent container exposed outside of the movable protective casing, the first and second clamping members each provided with at least one optical waveguide slot extending therethrough, each one of the optical waveguide slots substantially aligned with the portion of the translucent container exposed outside of the movable protective casing when the first and second clamping members are disposed in the analysis position to provide optical access to the portion of the translucent container exposed from the movable protective casing for optical analysis of the fluid sample in the translucent container.

In accordance with another broad aspect, there is provided a system for dynamic light scattering of the fluid sample contained within the translucent container, the system comprising: the sample holder described above, a light source for emitting light; a first optical waveguide connected to the light source and at least partially disposed within one of the optical waveguide slots of the first clamping member for propagating the light within the fluid sample when the first clamping member is in the analysis position; one or more second optical waveguides each at least partially disposed within a respective one of the optical waveguide slots of the second clamping member for collecting light scattered by the fluid sample when the second clamping member is in the analysis position; and one or more light detectors each connected to a respective one of the second optical waveguides for measuring light collected by the respective second optical waveguide.

In accordance with another broad aspect, there is provided a sampling set for sterile extraction of a fluid sample from a biological fluid storage reservoir for optical analysis of the fluid sample, the sampling set comprising: a sample holder having a pair of clamping members disposed on opposite sides of an opening, the clamping members being rotatable between a container accepting position and an analysis position, the clamping members each having at least one optical waveguide slot extending therethrough, the optical waveguide slots being substantially aligned to intersect within the opening when the clamping members are disposed in the analysis position; a fluid container assembly having an inlet adapted to be connected to the fluid storage reservoir and an analysis end in fluid flow communication therein, the analysis end being received within the opening of the sample holder and including a translucent container enclosed within a moveable protective case, the translucent container receiving the fluid sample therein, the protective case being displaceable between a closed position in which the translucent container is fully protected by the protective case and an open position in which at least a portion of the translucent container is exposed outside of the protective case; and wherein the rotation of the clamping members of the sample holder from the container accepting position to the analysis position displaces the protective case of the fluid container assembly from the closed to the open position thereof, such as to permit optical analysis of the fluid sample within said exposed portion of the translucent container via the substantially aligned optical waveguide slots.

In accordance with a further broad aspect, there is provided a fluid container assembly for a biological fluid to be tested by optical analysis by a biological testing instrument, the sampling device comprising: a body defining a conduit extending therethrough between an inlet end adapted to be connected to the fluid reservoir and an analysis end, the analysis end being adapted to be inserted within a sample holder for optical analysis of the biological fluid; and the analysis end including a translucent container enclosed within a moveable protective case, the protective case being displaceable between a protective position in which the translucent container is fully enclosed by the protective case and an analysis position in which at least a portion of the translucent container is exposed outside of the protective casing such as to permit optical analysis of a test sample of the biological within said portion of the translucent container.

BRIEF DESCRIPTION OF THE DRAWINGS

Further features and advantages of the present invention will become apparent from the following detailed description, taken in combination with the appended drawings, in which:

FIG. 6 is a front view of an apparatus for dynamic light scattering analysis having a fluid container assembly disposed therein, in accordance with an embodiment;

FIG. 7 is a top view of the apparatus of FIG. 6;

FIG. 9a is a schematic illustration of a fluid container assembly comprising a piston valve in a closed position, in accordance with an embodiment;

FIG. 9b is a schematic illustration of the fluid container assembly of FIG. 9b in an open position;

FIG. 13 schematically illustrates the sample holder of FIG. 12 with the clamping members partially see-through;

FIG. 17 schematically illustrates the sample holder of FIG. 16 with the clamping members partially see-through.

It should be noted that throughout the appended drawings, like features are identified by like reference numerals.

DETAILED DESCRIPTION

Figure 1:
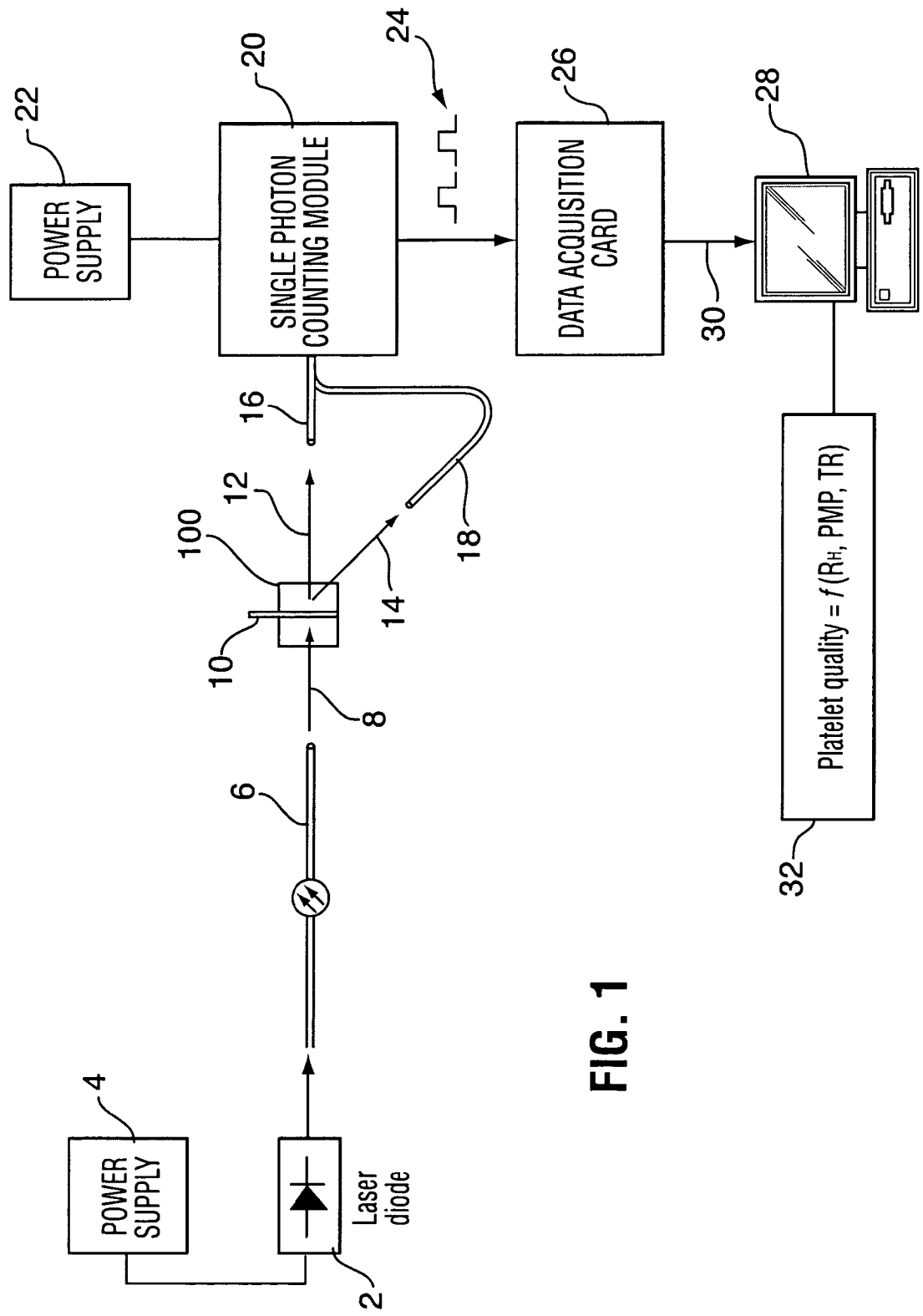
FIG. 1 is a schematic view of a DLS system having a sample holder in accordance with an embodiment of the present invention.

FIG. 1 is a schematic view of a system for dynamic light scattering (DLS), which is also known as quasi-elastic light scattering (QELS). As shown in FIG. 1, the system has a light source such as, for example, a laser diode 2 which is powered by a power source, as is well known in the art. The laser diode 2 generates and emits a beam of laser light into a length of optical fiber 6. The laser preferably generates light at 635 nm although other wavelengths could be used, as would be appreciated by those of ordinary skill in the art. As is also known in the art, the intensity of the laser beam can be adjusted using an adjustable neutral density filter (or by using an attenuator in the fiber) which allows the laser to be operated at maximum power while curtailing the intensity of the incident light. This reduces multiple scattering and other undesirable optical effects that arise when the intensity of the incident light is too high. The optical fiber can be single-mode, polarization-maintaining optical fiber which, as is well known in the art, prevents the polarization from drifting when the light propagates through the optical fiber or, alternatively, multimode fiber can be utilized. As is known in optics, polarization-maintaining fibers can be made using fibers of noncircular cross-section or by making the propagation medium of the fibers anisotropic such as, for example, by stressing the fibers in a specific direction.

As shown in FIG. 1, the polarized laser light emerges from the optical fiber 6 and travels a short distance through the air (although it should be expressly understood that the distances shown in FIG. 1 are not meant to be representative or proportional to actual distances). This incident light impinges on a fluid sample (e.g. platelets in suspension, whole blood, or other colloids or colloidal dispersions) contained with a transparent or translucent container 10 (e.g. a capillary, cuvette, tube or like structure) held by a sample holder 100 in accordance with embodiments of the present invention. The sample holder 100 will be described in greater detail below with reference to FIGS. 3-5.

As shown in FIG. 1, the incident light scatters when photons strike particles suspended in the solution. The scattered light 12, 14 scatters in various directions away from the fluid sample. A portion of this scattered light is collected by light collectors 16, 18, which are preferably optical fibers connected to a single-photon counting module 20 powered by power supply 22. It is of note that although two power supplies 4 and 22 are depicted in FIG. 1, these two power supplies can in fact be one and the same. Thus, in a particular embodiment of the system, a single power supply is used to power both the single-photon counting module 20 and the laser diode 2. In a preferred embodiment, the single-photon counting module 20 generates TTL pulses (transistor-transistor logic pulses) 24 and transmits these TTL pulses 24 to a data acquisition card 26. The data acquisition card 26 digitizes the TTL pulses and communicates the "raw data" to a software correlator running on a laptop or other computer 28. This raw data is communicated via a universal serial bus (USB) 30 or other data bus or connector. Alternatively, the data acquisition card 26 can be installed within the computer 28. Together, the data acquisition card 26, computer 28 and software correlator constitute a "correlating means", as this expression is used in the present specification. Alternatively, the correlating means could utilize a hardware correlator (e.g. a multi-tau correlator) instead of the data acquisition card. The hardware correlator would generate and communicate a correlation function to the computer, although the data acquisition card and software correlator are preferred as it has been found to be more accurate. Correlating the observed speckle pattern that arises due to Brownian motion with particle size (i.e. hydrodynamic radius) is based on the Stokes-Einstein equation, as is known in the art.

Figure 2:
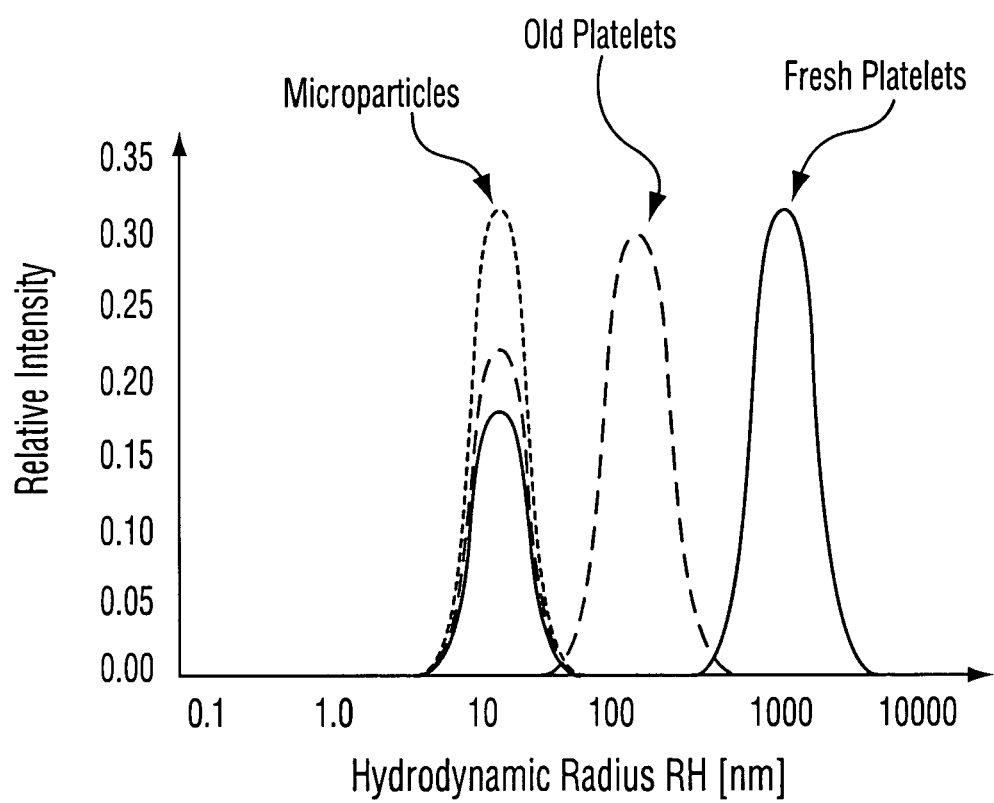
FIG. 2 is a graph plotting a distribution of hydrodynamic radii as a function of light intensity obtained from a DLS "speckle pattern" of platelets and platelet-derived microparticles (PMPs) in solution as could be obtained using the DLS system shown in FIG. 1.

The computer 28 (running the software correlator) generates a correlation function and then generates a size distribution plot, such as the one shown in FIG. 2, for graphical presentation to a researcher or other end-user. Alternatively, size distribution data can be presented in tabular form or in any other intelligible manner.

As depicted in FIG. 2, the size distribution plot shows a representative distribution of hydrodynamic radii for platelets and microparticles in a fresh platelet concentrate (solid line), platelets and microparticles in an old platelet concentrate (dashed line) and platelet-derived microparticles alone (PMPs) (dotted line) although it should be expressly understood that the hydrodynamic radii, relative intensities and particle distributions shown are not meant to represent actual values or distributions. The hydrodynamic radii are calculated from the DLS "speckle pattern", as is known in the art. The size distribution plot readily enables researchers, technicians or other end-users to evaluate platelet quality and viability by virtue of the size distribution. New platelets can be distinguished from old platelets because the mean hydrodynamic radius ($R_H$) of platelets diminishes with age. Likewise, platelet-derived microparticles (PMPs) serve as a second useful indicator of age (and diminishing platelet quality) because PMPs form, or "bud off", as platelets degrade over time. Temperature response is yet another means of evaluating platelet age and quality: fresh platelets can be prepared such that they are more (or less) resistant to temperature variation than old platelet concentrates.

In one embodiment, the computer 28 implements a computational matrix 32 for analyzing platelet quality and viability based on three independent factors, namely (i) the mean hydrodynamic radius of the platelets, (ii) the relative number of PMPs and (iii) the platelet response to temperature cycling. As shown in FIG. 1, the computational matrix 32 quantifies platelet quality as a function of mean hydrodynamic radius ($R_H$), PMP concentration, and temperature response (TR). The computational matrix 32 therefore enables automated platelet scoring because the system can simultaneously measure and input into the computational matrix all three of these independent parameters, thus providing very high analytic sensitivity for platelet quality determinations. This methodology is described in detail in applicant's U.S. Pat. No. 7,341, 873 (Maurer) entitled METHOD FOR DETERMINATION OF PLATELETS QUALITY, which is hereby incorporated by reference.

It should be expressly understood that this system can be used not only for DLS analysis of platelets in solution, but also for analyzing whole blood or other colloids or colloidal dispersions.

Figure 3:
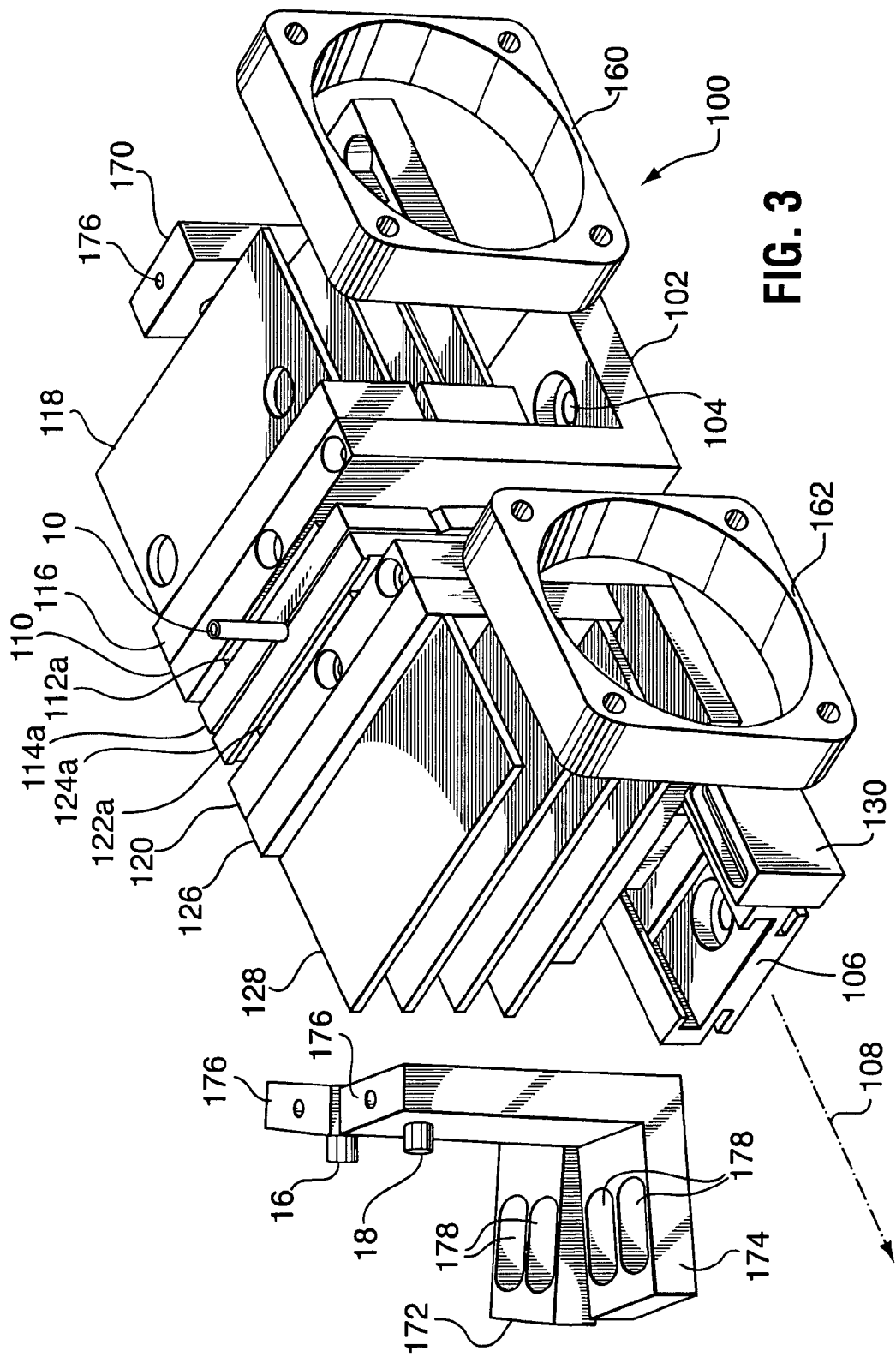
FIG. 3 is an isometric perspective view of a sample holder in accordance with a preferred embodiment of the present invention, shown in the closed, gripping position.

FIG. 3 illustrates the sample holder 100 in accordance with a preferred embodiment of the present invention. The sample holder 100 (also referred to herein as a sample-holding device) has a stationary base 102 which has a substantially flat underside for sitting upon a flat surface such as a workbench, lab counter, table, base plate or the like. The base preferably includes one or more bores through which a fastener could be inserted to securely mount the base to a base plate, table, workbench, lab countertop or the like. It is preferable that the base 102 of the sample holder 100 be securely attached to an immovable structure to improve measurement precision and to avoid having to frequently recalibrate the DLS system.

The base 102 preferably includes a rectilinear rail 106 defining a displacement axis 108. For manufacturability, the rail 106 and base 102 are preferably machined or cast as separate components and secured to each other by threaded fasteners (to thus define a "two-part base"). Alternatively, it would also be possible for the rail 106 to be made integral with the base 102 (to define a unitary base). In any event, the base 102 has a connected rail portion 106 that together supports the rest of the sample holder.

The sample holder 100 further includes an upright backing member 110 (i.e. a fixed, upright wall) and a movable clamping member 120 (i.e. a movable upright member) that can move relative to the backing member (or wall) 110 between an open, retracted position, in which the clamping member 120 no longer contacts the container 10 (i.e. the movable upright member and the wall are separated by a distance greater than an outer diameter of the container 10) and a closed, holding (or "gripping") position, in which the clamping member (movable upright member) 120 presses against the container 10 to lightly and gently clamp or hold the container 10 between the clamping member 120 (movable member) and the backing member (wall) 110 whereby the container 10 is immobilized for optical analysis of the fluid sample in the container 10. While the illustrated embodiments of the sample holder were designed for optical analysis such as DLS or QELS, the sample holder (or variants thereof) can also be used for static light scattering or as part of a spectrofluorometer. Preferably, the backing member 110 is integral with the base 102. Similarly, in the preferred embodiment, the movable member 120 is integrally formed with a horizontally disposed sliding plate 120a that engages and slides over the rail 106.

In a preferred embodiment, the movable upright member 120 slides relative to the stationary wall member 110, guided by the rail 106 so that the movable member 120 is constrained to translate along the displacement axis 108. The displacement axis 108, as shown in FIG. 3, is substantially perpendicular to the backing and clamping members 110, 120. While sliding, or translational, motion is preferred, the movable upright member 120 could also be made to rotate relative to the wall 110 using pivots or hinges. The movable upright member 120 could also be made to slide along a vertical axis or a different horizontal axis, i.e. an axis orthogonal to the illustrated displacement axis 108. Alternatively, the sample holder 100 could use compound motion (both rotation and translation) to open and close the clamping member relative to the fixed, upright wall member.

Figure 5:
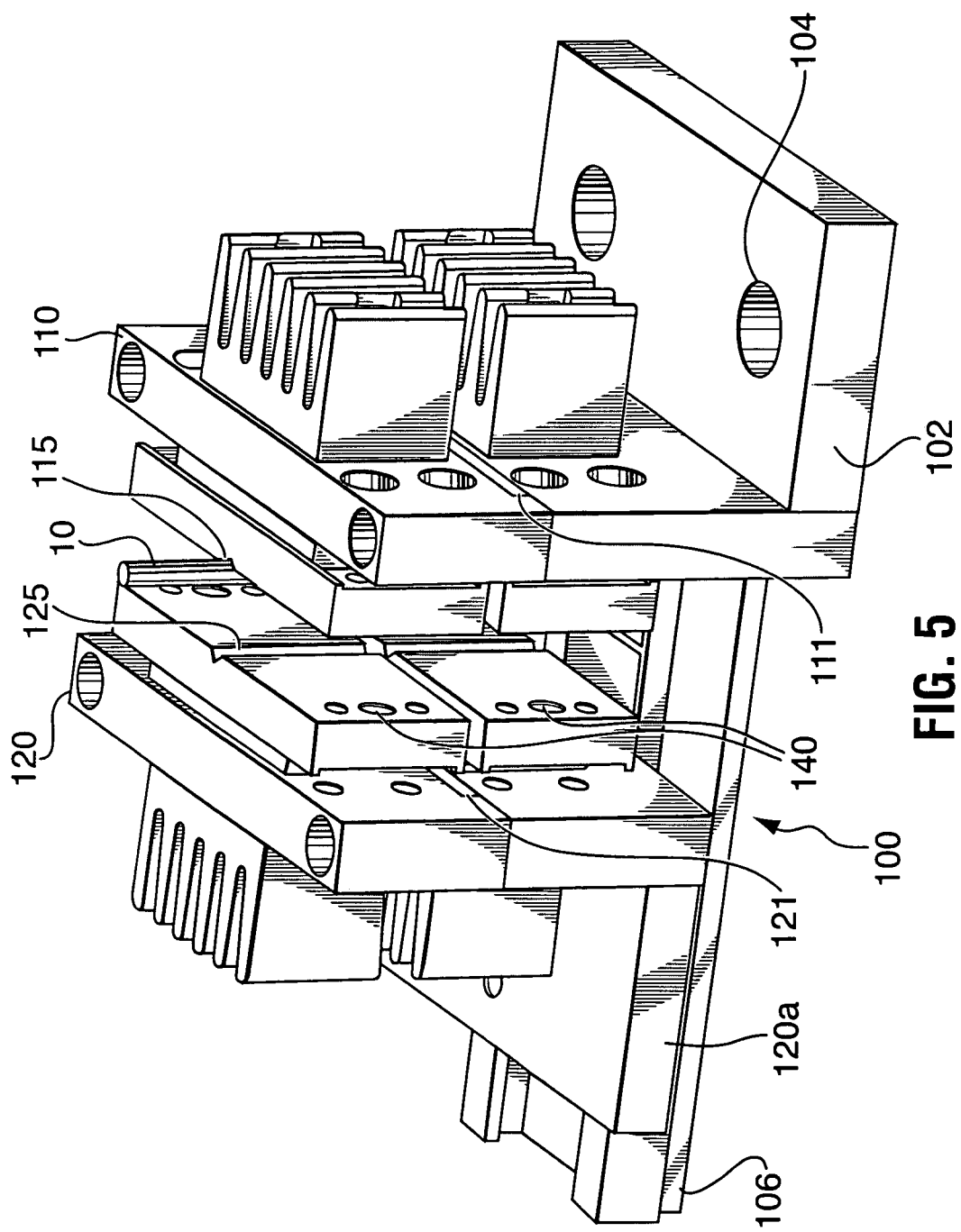
FIG. 5 is an isometric perspective view of the sample holder in accordance with another embodiment of the invention, shown in the open, retracted position.

The sample holder can further include a plurality of magnets 140 for biasing the movable member 120 toward the wall 110. Preferably, four pairs of cylindrical, oppositely poled magnets 140 are embedded in bores in the movable member (as shown in FIG. 5) and in the wall which thus provide a uniform magnetic force of attraction in substantial alignment with the displacement axis 108. The magnets 140 are designed to generate a magnetic force of attraction that, when the movable upright member is in the gripping position, is large enough to securely hold the container between the movable upright member and the wall but small enough to preclude deformation of the container and also small enough to enable a user to easily manually separate the movable upright member and the wall by manually forcing the movable upright member to the retracted position.

As shown in FIG. 3, the sample holder 100 can include a slider stopper 130, which can be secured to the rail 106 (or to the base plate) using one or more threaded fasteners (not shown). The slider stopper 130 limits the sliding displacement of the movable member 120 away from the wall 110. When the movable member reaches the slider stopper 130, the movable member is in the open, retracted position (which is shown in FIG. 5).

Figure 4:
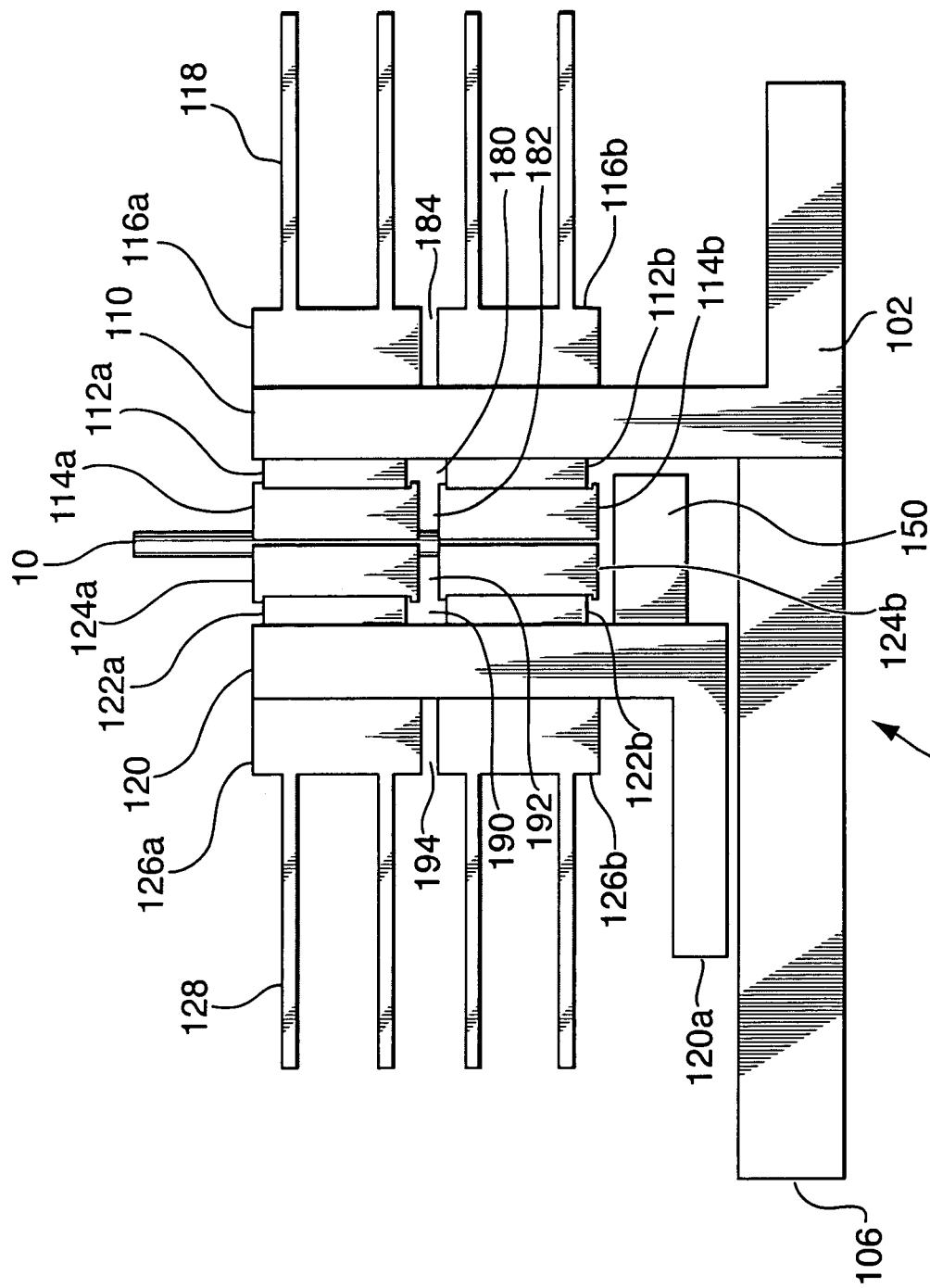
FIG. 4 is a side view of the sample holder shown in FIG. 3, but illustrated without the fans and fiber-holding brackets, also shown in the closed position.

FIG. 4 is a side elevational view of the sample holder 100 shown in FIG. 3, but depicted without the fans and fiber-holding brackets. As shown in FIGS. 3 and 4, the sample holder 100 has a first pair of vertically spaced-apart heating/cooling elements 112a, 112b connected to an inwardly facing surface of the backing member 110, the first pair of heating/cooling elements being capable of transferring heat to or from the fluid sample in the container 10. For the purposes of this specification, "vertically spaced-apart" means that there is an upper component and a lower component separated by a gap. Also for the purposes of this specification, "inwardly facing" means facing toward the sample container and thus "outwardly facing" means facing away from the sample container.

The sample holder 100 also includes a first pair of vertically spaced-apart heat-conductive plates 114a, 114b connected to inwardly facing surfaces of the first pair of heating/cooling elements 112a, 112b for conducting heat to or from the container to thus either cool or heat the fluid sample.

The sample holder 100 further includes a second pair of vertically spaced-apart heating/cooling elements 122a, 122b connected to an inwardly facing surface of the movable clamping member 120, the second pair of heating/cooling elements being capable of transferring heat to or from the fluid sample in the container 10. The sample holder 100 further includes a second pair of heat-conductive plates 124a, 124b connected to inwardly facing surfaces of the second pair of heating/cooling elements 122a, 122b for conducting heat to or from the container 10 to thus cool or heat the fluid sample. The heating/cooling elements can be attached to the movable member using studs and bores, threaded fasteners or other known mechanical fasteners. Likewise, the heat-conductive plates can be attached to the heating/cooling elements using studs and bores, threaded fasteners or other known mechanical fasteners.

To recap, therefore, there are four heating/cooling elements 112a, 112b, 122a, 122b and four attached plates 114a, 114b, 124a, 124b in the preferred embodiment, as shown in FIG. 4. The vertically spaced-apart pairs of heating/cooling elements define first gaps 180, 190. The vertically spaced-apart pairs of plates likewise define second gaps 182, 192. The first gaps 180, 190 are aligned with the second gaps 182, 192, as shown in FIG. 4. Furthermore, the wall 110 and the movable member 120 have substantially horizontal slots 111, 121 that also align with the gaps 180, 190, 182, 192 on either side of the device to minimally obstruct optical access to the fluid sample in the translucent container 10. Furthermore, as shown in FIG. 4, the sample holder 100 has upper and lower heat sinks 116a, 116b attached to the outwardly facing surface of the wall 110 as well as upper and lower heat sinks 126a, 126b attached to the outwardly facing surface of the movable member 120. The heat sinks can be attached to the wall and movable member using studs in bores, threaded fasteners or other known mechanical fasteners. As shown in FIG. 4, the upper heat sinks 116a, 126a are disposed above the slots 111, 121 in the wall 110 and movable member 120 while the lower heat sinks 116b, 126b are disposed below the slots 111, 121. This heat sink design also minimally obstructs optical access to the fluid sample in the container 10. These upper and lower heat sinks define on each side of the device third gaps 184, 194 which are also aligned with the first gaps 180, 190, the second gaps 182, 192 and the slots 111, 121.

Preferably, the heating/cooling elements 112, 122 are Peltier-type thermoelectric devices with microthermocouples for temperature sensing and feedback control. Peltier heater/cooler devices are also known in the art as thermoelectric modules. These Peltier-type thermoelectric modules are small solid-state devices that function as heat pumps. Usually, a Peltier device has a "sandwich" structure formed by two ceramic plates with an array of small Bismuth Telluride cubes ("couples") in between. When a DC current is applied to the device, heat is transferred from one side to the other, where it must be removed with a heat sink. By placing the "cold" side facing the heat-conductive plate, the sample can thus be cooled. If the current is reversed, the Peltier device heat is transferred to the inner side and this heats the sample. These Peltier thermoelectric modules enable the sample holder 100 to rapidly control the temperature of the sample, e.g. for bringing the sample to the desired temperature and for performing temperature cycling.

As noted above and shown in FIGS. 3 and 4, the sample holder 100 preferably includes heat sinks 116, 126 connected to outwardly facing surfaces of the wall and movable member, respectively. These heat sinks 116, 126 can include fins 118, 128, respectively. The fins can be horizontal (as shown in the embodiment of FIGS. 3 and 4) or vertical (as shown in the embodiment of FIG. 5). In any event, the finned heat sinks cooperate with the Peltier devices to cool the fluid sample by drawing heat away from the hot side of the Peltier devices.

In a preferred embodiment, the sample holder 100 includes fans 160, 162 for further improving the cooling efficiency of the Peltier devices by augmenting convective heat transfer of the finned heat sinks. It should be noted that the fans could be part of the sample holder 100 or they could be separate components (but nonetheless part of the DLS system). It should be noted that it is preferable to have the fans to improve cooling efficiency but they are not essential.

As further shown in FIG. 3, the sample holder can include a plurality of fiber-holding brackets 170, 172, 174 for holding the optical fibers at the same height as the slots to ensure that the incident light hits the sample and that the scattered light from the sample can be captured by the light-collecting fibers 16, 18. The optical fibers have either a focusing or collimating lens to narrow the laser beam so that illuminated sample volume is small, i.e. ideally one or only a few coherence volumes. This requires the ends of the optical fibers to be one focal length away from the center of the sample. The fiber holders 170, 172, 174 are thus mounted relative to the sample in order to provide distances to the sample that are each equal to the focal length. In a preferred embodiment, a first L-shaped bracket 170 holds the optical fiber 6 connected to the laser diode 2 or other optical source (referring back to FIG. 1) whereas second and third L-shaped brackets 172, 174 hold the light-collecting fibers 16, 18, respectively. Other brackets would, of course, be provided if additional light-collecting fibers are to be used to capture scattered light. As shown in FIG. 3, each of the L-shaped brackets includes a top threaded bore 176 for receiving a set screw (not shown) which can be used to fix the optical fiber in the bracket to ensure alignment with the plane of the slots. As shown in FIG. 3, each of the L-shaped brackets also includes a footing with an oblong slot through which a fastener can be inserted to secure the brackets to a bench, table, counter, base plate or other such surface.

In this embodiment, only a single light source is used and scattered light is collected by a plurality of light collectors. For example, the light collectors can be spaced at 15-degree intervals from each other. In one configuration, one light collector could be set up at a 45-degree angle from the incident light with a second collector at a 60-degree angle (again with respect to the incident light). Alternatively, the light collectors (or additional collectors) could be set up at 30 and 90 degrees. However, it should be appreciated that multiple light sources could be used as well and the number of light collectors and their respective angles or positions could also be varied. The sample holder 100 therefore enables a researcher to simultaneously obtain measurements at one or more scattering angles.

As further shown in FIG. 4, the sample holder 100 can include an elevated footrest 150 securely connected to a bottom portion of the movable member 120. In one embodiment, the footrest 150 can be detachable or vertically adjustable to accommodate capillaries or cuvettes of different lengths. In another embodiment, the footrest could include its own heating/cooling element (e.g. Peltier device) to supplement the heating/cooling elements 112, 122 already described above.

FIG. 5 illustrates the sample holder 100 in accordance with another embodiment of the present invention, shown in the open, retracted position. FIG. 5 shows that the backing member 110 and the clamping member 120 include, respectively, first and second grooved plates 114, 124 facing each other in a generally parallel arrangement and having opposed, substantially vertical grooves 115, 125 for holding the fluid container 10 in a substantially vertical orientation. The plates 114, 124 could also have knurling or other surface finishing that enhances adherence to glass or plastic so as to promote gripping of the glass or plastic capillaries or cuvettes. As shown, the grooves 115, 125 could have V-shaped profiles to grip a variety of differently sized, elongated tubular or square containers, such as capillaries or cuvettes. V-shaped grooves are generally preferred because they promote excellent heat transfer to or from a variety of differently sized and differently shaped containers. Alternatively, the grooves could have semicircular or rectangular profiles to grip capillaries or cuvettes having substantially round or substantially square cross-sections. To optimize heat transfer efficiency, the grooves should provide a substantially exact fit with the capillary or cuvette, although an exact fit is of course not necessary. In other words, semicircular or rectangular grooves can also be used to hold variably sized containers. Preferably, the sample container 10 is a disposable, glass or plastic capillary with round or square geometry and having a diameter of about 2 mm and a volume of about 30 microliters, although the sample holder 100 is designed to accommodate a range of sizes and therefore these dimensions should not be considered as limiting the scope of the invention. As is known in the art, the sample is loaded by capillary action and then the bottom of the capillary is sealed. In one embodiment, the V-shaped grooves are adapted to grip a capillary having an outer diameter in a range of 1.7 to 3.5 mm.

A further advantage of this sample holder 100 is that the path length of the light is short compared to most prior art devices because both the light path through the air, the wall thickness and the diameter of the capillary or cuvette are reduced. A short path length is desirable for measuring highly concentrated samples because this diminishes the likelihood that scattered light will strike a second particle and be scattered a second time (a phenomenon known as "multiple scattering"). In the context of platelet quality management, improving measurement precision means that it is easier to determine when a platelet solution is still viable and when it is no longer effective. It also advantageously reduces handling since platelet solutions need not be diluted prior to measurement.

In another embodiment, which is not illustrated, the sample holder could have two movable and lockable members rather than one movable member and a stationary wall. In this embodiment, one of the movable lockable members is locked in place, the container placed in the sample holder next to the locked movable member and then the second (unlocked) movable member is then moved into engagement with the container to thereby hold the container in place at which point the second (unlocked) movable member can be locked as well.

Fresh platelets can be prepared such that they are more (or less) resistant to temperature variation than old platelet concentrates.

Referring now to FIGS. 6 and 7 which illustrate a sample holder 300 in accordance with another embodiment. The sample holder 300 is used with a DLS apparatus for testing of a fluid sample contained within a fluid container assembly 200, shown in FIG. 8, which is received within the sample holder 300 for performing DLS analysis of the fluid sample within the fluid container assembly 200.

As will be described in further detail below, the fluid container assembly 200 which is received within the sample holder 300 for testing of the fluid sample comprises generally a translucent fluid sample container enclosed within a movable protective casing, and a suction device for drawing fluid from a reservoir, such as a platelet bag when the DLS system is being used to determine blood platelet quality prior to transfusion for example, into the translucent sample container. The DLS apparatus comprises an automated sample holder 300 for receiving the translucent sample container of the fluid container assembly 200, a light source, a first optical waveguide connected to the light source for illuminating the sample fluid contained in the translucent container, a second optical waveguide for collecting the light scattered by the sample fluid, and a light detector connected to the second optical waveguide for measuring the light collected by the second optical waveguide. The light detector is connectable to a correlator adapted to generate a correlation function and generate a size distribution plot, as described above.

Figure 8:
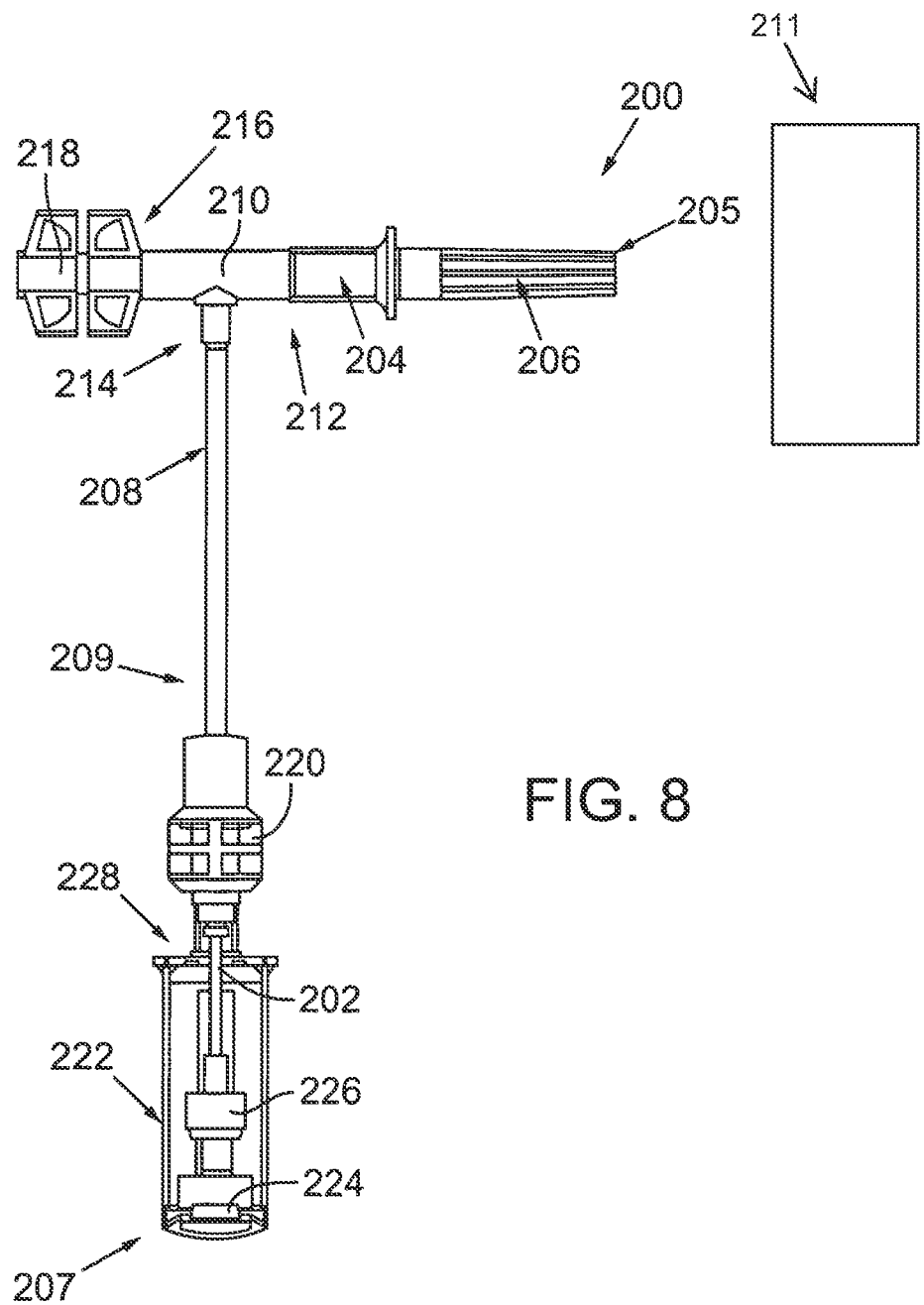
FIG. 8 illustrates a fluid container assembly comprising a bellows, in accordance with an embodiment.

Referring now to FIG. 8 which illustrates the fluid container assembly 200 that is received within the sample holder 300 for DLS testing using a DLS system (see FIG. 1 for example). The fluid container assembly 200 comprises generally a body 209 extending between an inlet end 205 which is adapted to be connected to a fluid source or reservoir 211, for example the aforementioned platelet bag, and an analysis end 207 which is received within the sample holder 300 for testing for the fluid sample. A conduit extends through the fluid container assembly 200 from the inlet end 205 to the analysis end 207, such that a small test sample of the fluid from the fluid reservoir 211 can be extracted by the assembly, as will be described, and retained in the analysis end 207 for testing by the DLS system. The analysis end 207, which is received within the sample holder 300 for optical analysis of the fluid sample, includes a translucent and/or transparent fluid sample container 202 which is enclosed within a movable protective casing 222. As will be seen, the protective casing 222 is displaceable between a protective position, wherein the translucent fluid container 202 is fully enclosed by the protective casing 222, and an exposed analysis position, wherein at least a portion of the translucent fluid container 202 is exposed outside of the protective casing such as to permit optical analysis, such as by DLS, of the fluid test sample within the fluid container 202.

The translucent and/or transparent fluid container 202 may include a translucent capillary, cuvette, tube, or the like. The term translucent container as used herein is intended to encompass any container that permits light, and particularly laser light, to pass therethrough such that the fluid within the container 202 can be tested using a DLS system which directs a laser through the container 202, and then collects the scattered light after having passed through the fluid contained therein. The container 202 may therefore be entirely transparent, entirely translucent or anywhere in between.

The inlet end 205 of the fluid container assembly 200 includes a spike 204 provided with a cap 206, which is connected in fluid flow communication with the translucent fluid container 202 of the analysis end 207 via a tube 208 and a T-connector 210. The T-connector 210 comprises three inlets/outlets 212, 214, and 216 fluidly connected together so that a fluid may flow from one of the three inlets/outlets 212, 214, and 216 to any one of the other inlets/outlets 212, 214, and 216. The inlets/outlets 212, 214, and 216 are fluidly connected to the spike 204, a port 218, and the tube 208, respectively.

A grip element 220 is secured to the tube 208 adjacent to the analysis end 207. The grip element 220 is used for removably securing the sample container assembly 200 to the sample holder 300. The grip element 220 may be positioned at any adequate location on the fluid container assembly 200, allowing the fluid container assembly 200 to be grasped for insertion and removal from the sample holder 300. Alternatively, the fluid container assembly 200 may comprise no grip element 220, and the T-connector 210 may be used to removably secure the fluid container assembly 200 to the sample holder 300.

As noted above, the analysis end 207 of the fluid container assembly 200 comprises a movable protective casing 222 sized and shaped to fully contain the translucent container 202. The protective casing 222 is movable with respect to the translucent container 202 and the grip element 220 between a closed or protective position (shown in FIG. 8) and an open or analysis position. When it is disposed in the closed position, the protective casing 222 is removably secured to the body 209 of the fluid container assembly 200 and the translucent container 202 is fully enclosed within the protective casing 220 and thereby protected, such as to prevent contamination or damage of the translucent container 202 and prevent it from become dirty (ex: from fingerprints, etc.) which could negatively influence the optical analysis of the fluid sample contained therein. When it is disposed in the open position, the protective casing 222 is spaced apart from the grip element 220 of the body 209 and at least a portion of the translucent container 202 is uncovered by the protective casing 222 such that it is sufficiently exposed for DLS analysis, as illustrated in FIG. 6.

In one particular embodiment, the protective casing 222, 256 is made from a completely opaque material, whereby the laser light of a optical analysis system, such as a DLS system, is not able to reach the fluid sample until such time as the protective casing 222 is withdrawn.

The analysis end 207 of the fluid container assembly 200 further comprises a bellows 224 contained within the protective casing 222. The bellows 224 has one end substantially hermetically secured to the translucent container 202 and another end substantially hermetically secured to the protective casing 222. The bellows 224 is shaped and sized to draw fluid into the translucent container 202 from the spike 204 at the inlet end 205 of the assembly. When the spike 204 is connected to a fluid sample reservoir, such as a fluid sample bag for example, and the sample holder 300 moves the protective casing 222 from the closed position to the open position thereof as will be described in further detail below, the bellows 224 are forced to stretch open (i.e. expand) which creates a vacuum within the fluid container assembly 200 thereby drawing fluid from the fluid sample reservoir into the translucent container 202, via the T-connector 210 and the tube 208.

Once the protective casing 22 is in the open or analysis position, it may remain in this position and the entire fluid container assembly 200 may be removed from the sample holder 300 after DLS testing of the fluid sample has been performed. However, in one possible embodiment, when the protective casing 222 is moved from the open position back to the closed position, the bellows 224 are compressed and the fluid contained within the translucent container 202 is expulsed via the spike 204 or the port 218, if opened. The fluid container assembly 200 comprising the bellows 204 therefore draws a fluid sample into the translucent container 202 for optical analysis, in a manner which allows for an automated drawing of fluid.

The fluid container assembly 200 may further comprise a one-way valve 226, positioned between the translucent container 202 and the bellows 224 to allow a flow of fluid only from the translucent container 202 towards the bellows 224. Since the one-way valve 226 prevents any flow of fluid from the bellows 224 into the translucent container 202, the protective casing 222, is prevented from moving from the open position to the closed position. The one-way valve 226 prevents back-flow from the bellows back into the translucent container 202, which helps to prevent the breach of sterility of the fluid sample within the translucent container 202. The one-way valve 226 may alternately be positioned at any other adequate location within the fluid container assembly 220 such as between the translucent container 202 and the tube 208, between the tube 208 and the T-connector 210, or the like.

The analysis end 207 of the fluid container assembly 200 can also be alternately connected to the tubing 208 of the body 209 by a sterile docking connection, whether permanently attached via a weld or other fastening means, or detachable connected by a mating interconnection. As such, in this alternate embodiment the parts upstream of the tubing 208, including the inlet end 205 having the spike 204 and the T-connection 210, etc., can be omitted.

While the present description refers to a grip 220 for removably securing the fluid container assembly 200 to the sample holder 300, it should be understood that any adequate securing means may be used. For example, a ring may be secured to the tube 208 adjacent to the translucent container 202 in order to removably secure the fluid container assembly 200 to the sample holder. The ring is larger than the opening of the sample holder 300 in which the translucent container is inserted so that the ring abuts the frame of the sample holder and maintains the protective casing and the translucent container within the sample holder. It should also be understood that the bellows 224 may be replaced by any adequate suction generating element or vacuum device which may, but need not necessary be, operable by the motion of the protective casing 222.

FIGS. 9a and 9b illustrate an alternate embodiment of a fluid container assembly 250 provided with a suction generating element in the form of a piston valve 252, in lieu of the bellows 224 described above. The fluid container assembly 250 comprises a translucent container 254 enclosable within a movable protective casing 256. The translucent container 254 has a first end fluidly connected to a tube 258 or any adequate body defining a conduit and connectable to a fluid reservoir, and a second end fluidly and fixedly connected to the piston valve 252. The piston valve 252 is positioned within the protective casing 256 and comprises a valve tube 260, a piston 262, and a plunger 264. The valve tube 260 is fixedly and fluidly connected to the second end of the translucent container 254 in order to have a fixed position with respect to the translucent container 254. The piston 262 has one end fixedly secured to the protective casing 256 and another end fixedly secured to the plunger 264 which is slidable within the valve tube 260.

The fluid container assembly 250 illustrated in FIG. 9a is disposed in a protective position, i.e. the translucent container 254 is fully enclosed within the protective casing 256. By downwardly pushing or pulling on the abutting portion 266 of the protective casing 256, the protective casing 256 is moved with respect to the translucent container 254. The motion of the protective casing 256 drives the motion of the plunger 264 which draws fluid into the translucent container 254 from a reservoir connected to the tube 258. As a result of the motion of the protective casing 256, at least a portion 268 of the translucent casing 254 is uncovered and exposed for DLS analysis.

In a further alternate embodiment, the fluid container assembly 200, 250 may comprise no suction device. In this case, the fluid to be analyzed in inserted into the translucent container 202, 254 before the insertion of the analysis portion of the assembly 200, 250 within the sample holder 300, i.e. before the insertion of the protective casing 222, 256 containing the translucent container 202, 254, respectively.

In a particular embodiment, the fluid container assembly 200, 250 described herein is a disposable sampling device for extracting a test sample of blood platelet concentrate from a platelet bag, for example.

Referring back to FIGS. 6 and 7, the sample holder 300 which receives the above-described fluid container assembly 200, as well as the interconnection therebetween, will now be described. The analysis end 207 of the fluid container assembly 200 is inserted in an opening 302 provided in the frame 304 of the sample holder 300. The protective casing 222 remains in its closed or protective position, whereby the translucent container 202 remains fully enclosed and protected therewithin. The grip element 220 is removably secured to the frame 304 of the sample holder 300. The sample holder 300 comprises first and second clamping members 306 and 308 positioned on opposite sides of the opening 302 within the frame 304. When the protective casing 222 of the fluid container assembly's analysis end 207, having the translucent container 202 disposed therein, is inserted into the sample holder 300, the first and second clamping members 306 and 308 are disposed in a container accepting position (see FIG. 12), i.e. they are spaced apart so that the protective casing 222 may slide therebetween.

The first and second clamping members 306 and 308 are subsequently movable from the container accepting position to an analysis position, in which the first and second clamping members 306 and 308 abut the top end 228 of the protective casing 222 (see FIG. 8), thereby displacing the protective casing 222 of the fluid container assembly 20 into the open position thereof, and therefore exposing at least a portion of the translucent container 202 outside of the protective casing 222. The functioning of the clamping members is illustrated in greater detail in FIGS. 12 to 18, described further below. In the embodiment depicted herein, the first and second clamping members 306 and 308 rotate in opposite directions (i.e. one clock-wise and one counter clock-wise) about parallel fixed axes that are spaced apart from each other. However, other movements of the first and second clamping members remain possible, such as linear translation along opposed L-shaped travel paths for example, when displaced from the container accepting position to the analysis position.

The sample holder 300 may further comprise part of a larger DLS system, and includes a first optical fiber 310 is connected to a laser 312 and extends through the first clamping member 206 in order to inject light generated by the laser 312 into the sample fluid contained in the translucent container 202 when the first clamping member 306 is disposed in the analysis position. A second optical fiber 314 is connected to a light detector such as photon counter for example, and extends through the second clamping member 308 in order to collect light scattered by the sample fluid contained within the translucent container 202 when the second clamping member is disposed in the analysis position. The light characteristics measured by the light detector 316 are sent to the correlator which generates a correlation function and a size distribution plot, as described above.

Figure 10:
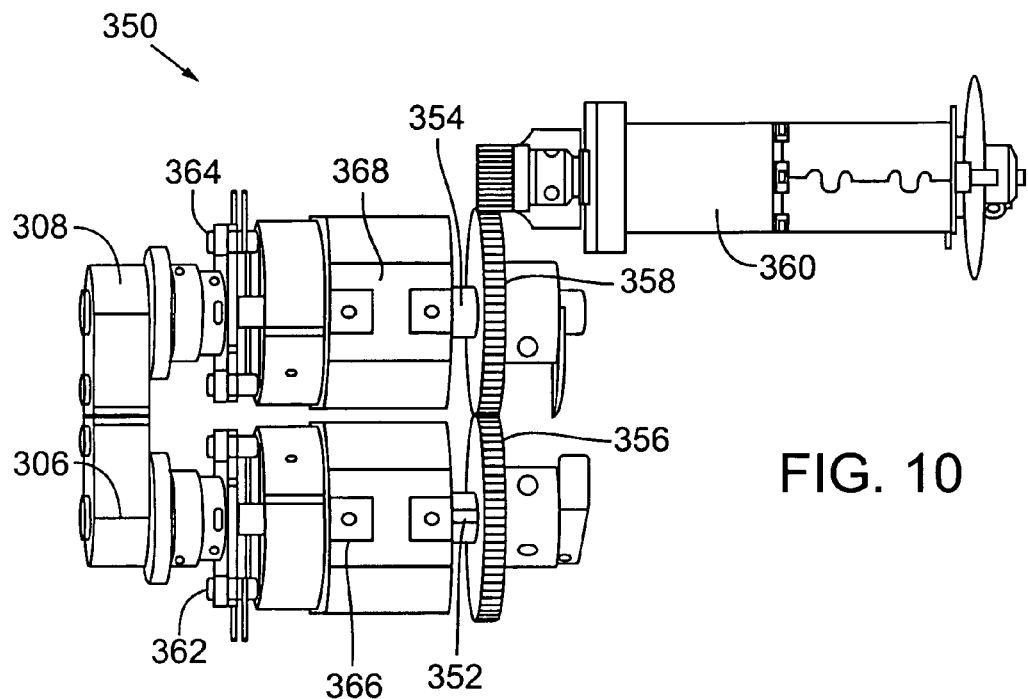
FIG. 10 is a top view of a motorized mechanism for driving clamping members of a sample holder, in accordance with an embodiment.
Figure 11:
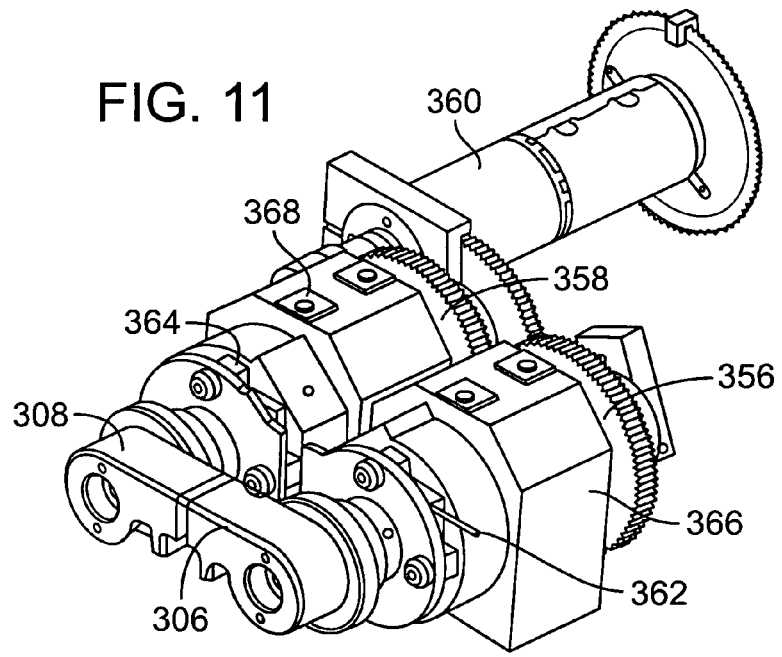
FIG. 11 is an isometric view of the motorized mechanism of FIG. 10.

FIGS. 10 and 11 illustrate one embodiment of a motorized mechanism 350 of the sample holder 300 for moving the first and second clamping members 306 and 308 between the container accepting position and the analysis position. The first and second clamping member 306 and 308 are connected to first and second shafts 352 and 354, respectively. A first gear wheel 356 is secured to the first shaft 352 for driving the first shaft 352 and rotating the first clamping member 306. A second gear wheel 358 operatively connected to the first gear wheel 356 is secured to the second shaft 354 for driving the second shaft 354 and rotating the second clamping member 308. A motor 360 operatively connected to the second gear wheel 358 is used for driving synchronously the first and second gear wheels 354 and 356. As a result, the actuation of the motor 360 drives an opposed and synchronous rotation of the first and second clamping members 306 and 308.

It should be understood that any adequate motorized mechanism adapted to move the first and second clamping members 306 and 308 between the container accepting position and the analysis position may be used. For example, each clamping member 306, 308 can be operatively connected to a respective motor. The motors may be actuated synchronously or asynchronously. While the present description refers to first and second clamping members 306 and 308 rotatable between the container accepting position and the analysis position, the clamping members may follow any adequate displacements such as translations, rotations, or any combinations thereof in order to move between the container accepting position and the analysis position.

The sample holder 300 may further comprise at least one heating/cooling element adapted to cool and/or heat the sample fluid contained in the translucent container 202 when the protective casing 222 is disposed in the analysis position and a portion of the translucent container 202 is exposed outside of the protective casing 222. In this case, the first and second members 306 and 308 are made of a thermally conductive material and may engage the portion of the translucent container 202 exposed outside of the protective casing 222 in order to improve the transfer of heat to or from the translucent container 202.

These heating/cooling elements may include, but need not necessarily be limited to, Peltier thermoelectric modules 362 and 364 thermally connected to the first and second clamping members 306 and 308, as illustrated in FIGS. 10 and 11. The Peltier modules 362 and 364 are also thermally connected to heat sinks 266 and 368, respectively, in order to cool their respective clamping member 306, 308. The Peltier modules 362 and 364, and the heat sinks 366 and 368 are mounted to the shaft 352 and 354, respectively, between the first and second clamping members 306 and 308, respectively, and the gear wheels 356 and 358, respectively.

FIGS. 12-18 schematically illustrate the cooperation between first and second clamping members 306, 308 of the automated sample holder 300 and the mating fluid container assembly 200, and in particular the protective casing 222 thereof, when the clapping members are moved from a container accepting position to an analysis position to clamp the fluid container assembly 200 in place within the sample holder 300 for optical testing, such as by the DLS system.

Figure 12:
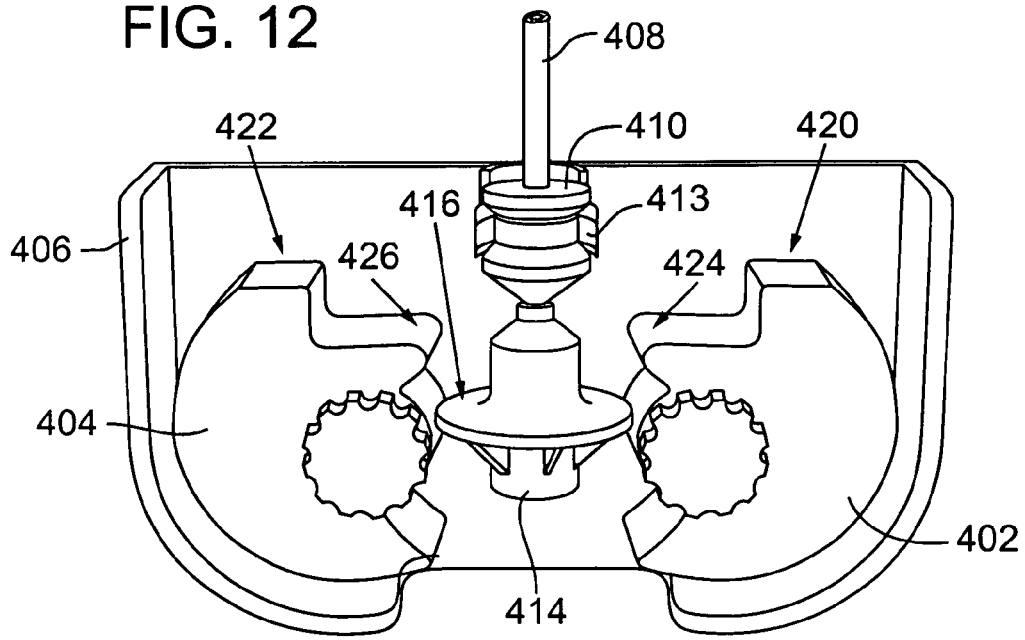
FIG. 12 schematically illustrates a sample holder having clamping members in a container accepting position and a translucent container fully disposed within a protective casing, in accordance with an embodiment.

FIG. 12 schematically illustrates a sample holder having first and second clamping members 402 and 404 disposed in a container accepting position. The clamping members 402 and 404 are rotatably secured to a frame 406 of the sample holder. A motorized mechanism (not shown) such as motorized mechanism 350 is operatively connected to the clamping members 402 and 404 for rotating the clamping members 402 and 404 between the container accepting position and an analysis position illustrated in FIG. 16.

A fluid container assembly is disposed within the sample holder between the first and second clamping members 402 and 404. The fluid container assembly comprises an elongated tube 408 having a first end fluidly connectable to a reservoir containing a fluid to be analyzed, a grip 410 fixedly secured to the tube 408, an elongated translucent container 412 fluidly connected to the tube 408 and enclosed within a movable protective casing 414. The movable protective casing 414 comprises an abutting portion 416 provided with a ring shape. The grip 410 is removably secured to the sample holder frame 406 via a clamp 413.

The clamping members 402 and 404 are positioned on opposite sides of the opening by which the protective casing 414 of the fluid container assembly is inserted. When disposed in the container accepting position, the clamping members 402 and 404 are spaced apart from the protective casing 414.

The first and second clamping members 402 and 404 each comprise a contacting portion 420 and 422, respectively, and a casing engaging portion 424 and 426. The casing engaging portions 424 and 426 are shaped and sized to engage the abutting portion 416 of the protective casing 414. For example, the casing engaging portions 424 and 426 may have a hook shape.

Figure 13:
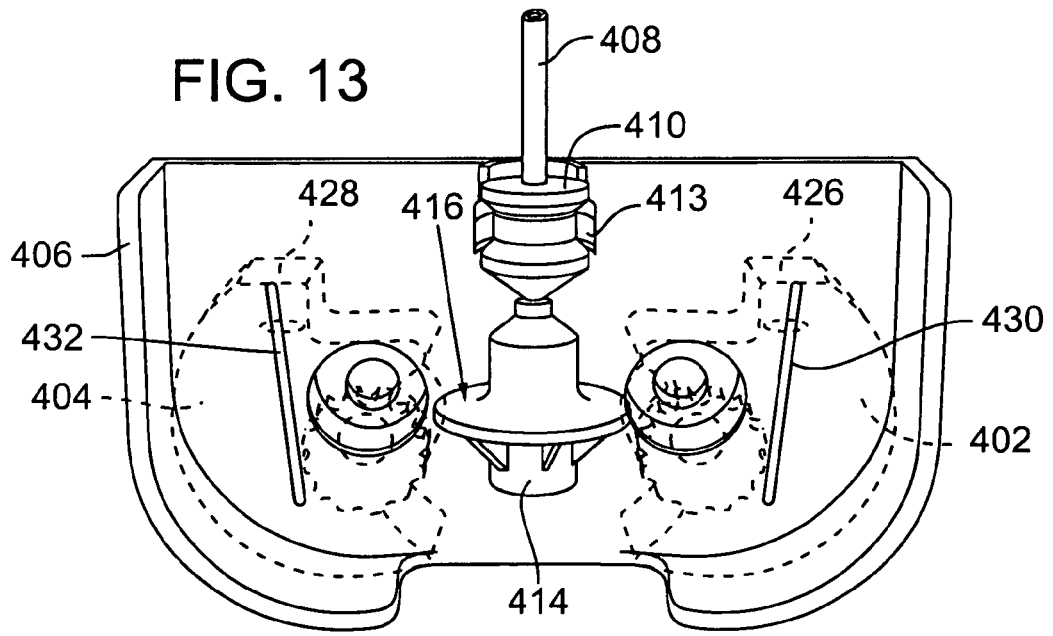

As illustrated in FIG. 13, the contacting portions 420 and 424 have a matching shape to engage one another and are each provided with a groove 426 and 428, respectively, sized and shaped to receive the translucent container 412. The contacting portions 420 and 424 are also each provided with a slot 430 and 432, respectively, extending therethrough. The slots 430 and 432 each have one end emerging in the groove 426 and 428, respectively. The slots 430 and 432 are sized and shaped to receive a respective optical waveguide such as the optical fibers 310 or 314 for example. Accordingly, these slots 430, 432 may be significantly wider than those shown in FIG. 13, for example.

Figure 14:
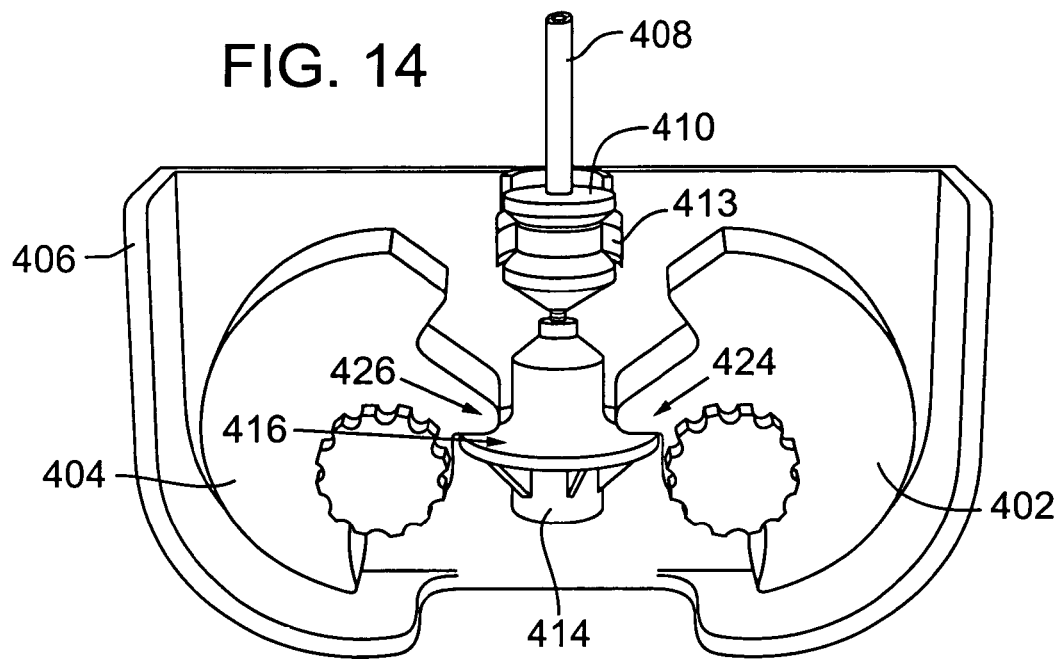
FIG. 14 schematically illustrates the sample holder of FIG. 12 having clamping members in a first intermediary position.
Figure 15:
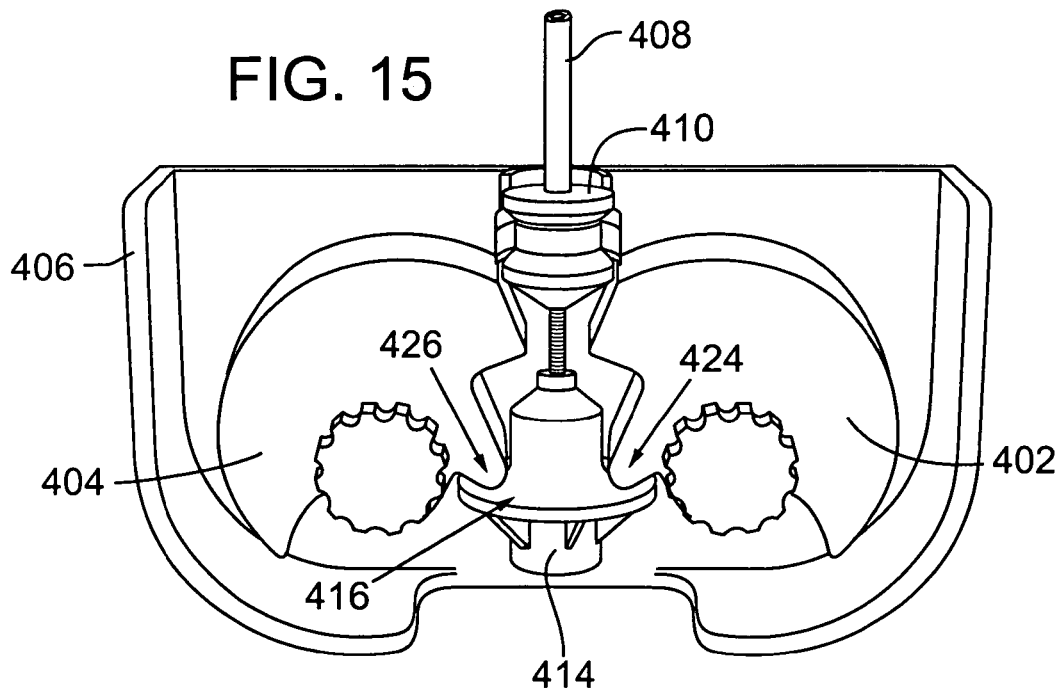
FIG. 15 schematically illustrates the sample holder of FIG. 12 having clamping members in a second intermediary position.
Figure 16:
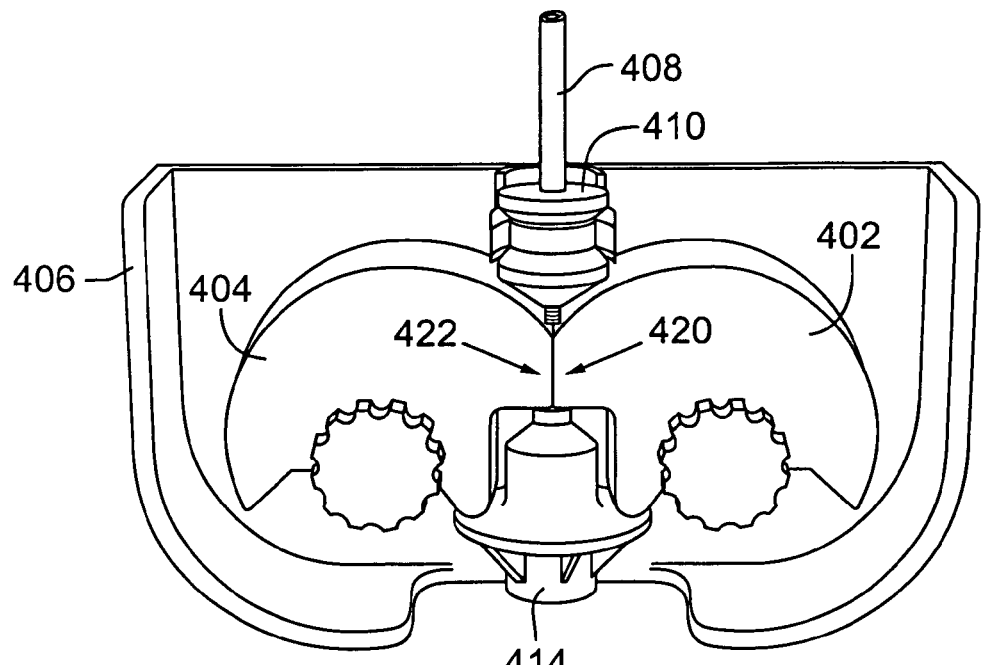
FIG. 16 schematically illustrates the sample holder of FIG. 12 having clamping members in an analysis position.
Figure 17:
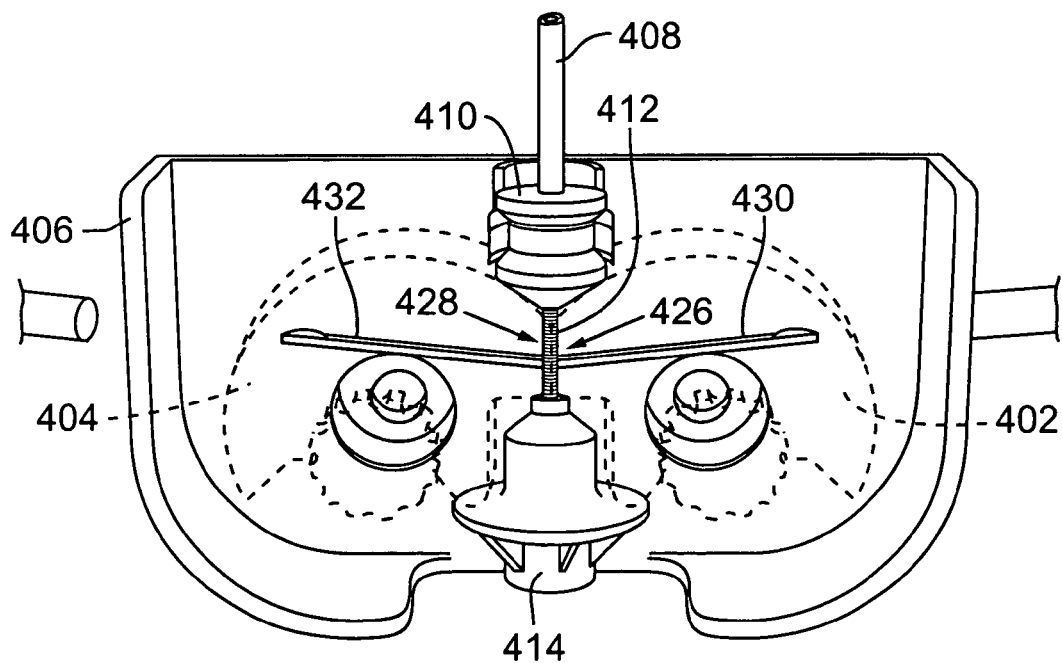

FIGS. 14-16 schematically illustrate the motion of the clamping members 402 and 404 from the container accepting position illustrated in FIGS. 12 and 13 to the analysis position illustrated in FIGS. 16 and 17. As illustrated in FIGS. 14 and 15, a rotation of the clamping members 402 and 404 expose a portion of the translucent container 412. The casing engaging portions 424 and 426 abut the abutting portion 416 of the protective casing 414 and downwardly move the protective casing 412 with respect to the translucent container 412 and the tube 408, thereby uncovering a portion of the translucent container 412.

FIGS. 16 and 17 illustrate the clamping members 402 and 404 in the analysis position. In this position, the contacting portions 420 and 424 contact each other and the grooves 426 and 428 form a channel in which the portion of the translucent channel 412 uncovered by the protective casing 414 is enclosed. The slots 430 and 432 emerge in the channel form by the grooves 426 and 428 so that an optical waveguide disposed within the slot 430 illuminates the a portion of the exposed translucent container 412 and another optical waveguide collects at least a portion of the light scattered by the fluid contained within the exposed translucent container 412.

Figure 18:
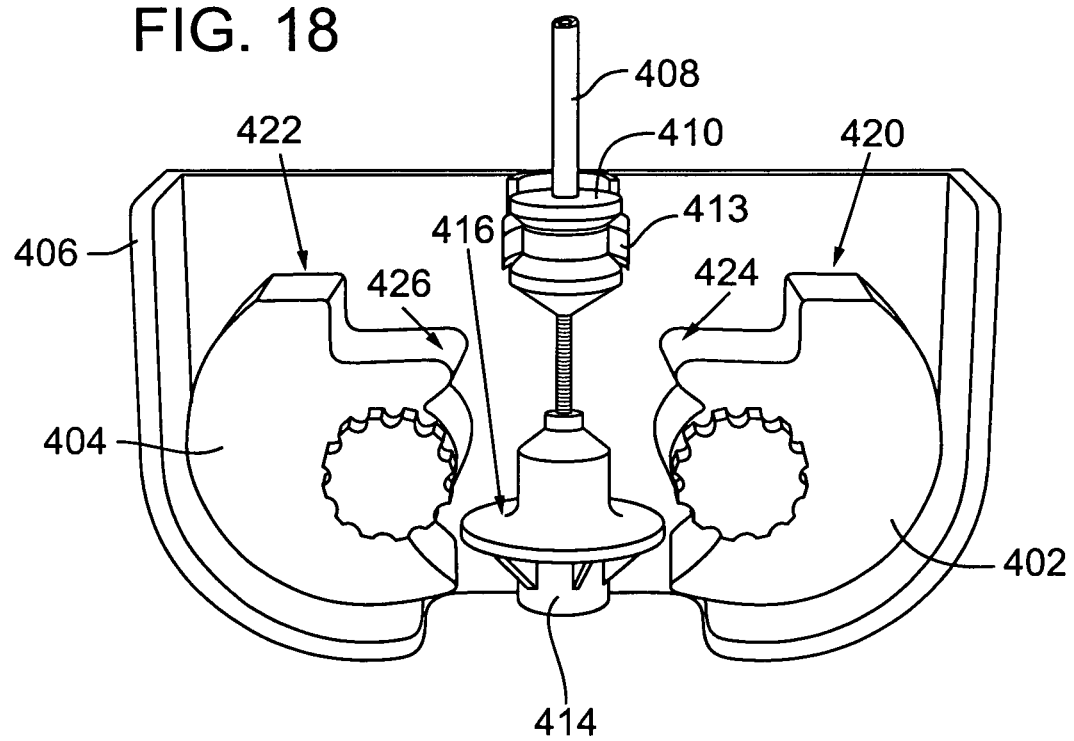
FIG. 18 schematically illustrates the sample holder of FIG. 12 having the clamping members in the container accepting position and the translucent container exposed, in accordance with an embodiment.

Once the DLS analysis of the fluid sample has been performed, the clamping members 402 and 404 are rotated back to the container accepting position, as illustrated in FIG. 18, and the fluid container assembly disposed in the open position can be removed from the sample holder.

As noted above, the fluid container assembly 200 may comprise a suction device fluidly connected to the translucent container 412 within the protective casing 414. In this case, the displacement of the clamping members 402 and 404 from the container accepting position to the analysis position actuates the suction device so that fluid is drawn from a reservoir fluidly connected to the tube 408 and into the translucent container 412, as the protective casing 414 is displaced from its closed, or protective, position to its open, or analysis, position.

In the depicted embodiment, the slots 430 and 432 are positioned within their respective clamping members 402 and 404 so that their respective axes each intersect the exposed translucent container 412 when the clamping members 402 and 404 are disposed in the analysis position, such that light can be directed through these slots 430,432 and through the fluid sample contained within the translucent container. The axes of the slots 430 and 432 may also intersect with the axis of the translucent container 412.

The slots 430 and 432 may be substantially aligned so that laser light can pass through one of the two slots to reach the fluid sample within the translucent container and such that the scattered light emanating out of the sample may pass through the other of the two slots for collection. Therefore, the term "substantially aligned" as used herein is intended to be defined in this manner. This may or may not mean, for example, that the axis of the two slots 430 and 432 are co-axial or are otherwise exactly aligned, provided that light can be transmitted serially therethrough when the clamping members 402 and 404 are disposed in the analysis position. In fact, in an alternate embodiment, the slots 430 and 432 are not coaxially aligned however their axes nonetheless intersect at an intersection point. The intersection point may be located along the axis of the translucent container 412.

Although the clamping members 402, 404 are shown in FIG. 13 as respectively having a single slot 430,432 through which the laser light is passed when the clamping members are in the closed, analysis, position, in an alternate embodiment at least one of the clamping members 402 and 404 may comprise more than one slot (ex: two slots) each receiving a respective optical waveguide for collecting light scattered by the fluid sample.

Although the grooves 426 and 428 engage the translucent container 412 when the clamping members are in the analysis position in the depicted embodiment, it is also possible however that a gap is left between the translucent container and the clamping members, such that no direct contact therebetween exists. The grooves 426 and 428 may be V-shaped to grip the elongated tubular container for example. In another example, the grooves 426 and 428 have a profile matching the cross-section of the translucent container. For example, the grooves 426 and 428 may have a rectangular or semicircular profile to grip a translucent container 412 having a substantially square or round cross-section, respectively.

While the present description refers to first and second clamping members 402 and 404 each provided with a casing engaging portion 424 and 426, respectively, it should be understood that only one of the two clamping members may comprise a casing engaging portion.

While the contacting portions 420 and 424 contact each other and engage the translucent container 412 when the clamping members 402 and 404 are disposed in the analysis position, it should be understood that other embodiments are possible. For example, the contacting portions 420 and 424 may be spaced apart while being adjacent to the translucent container 412 when the clamping members 402 and 404 are disposed in the analysis position. In another embodiment, the contacting portions 420 and 424 contact each other but do not contact the translucent container 412 when the clamping members 402 and 404 are disposed in the analysis position.

In another embodiment, the contacting portions 420 and 424 comprise no groove for receiving the translucent container 412. In this case, the contacting portions 420 and 424 may contact the translucent container 412 when the clamping members 402 and 404 are disposed in the analysis position. Alternatively, the contacting portions 420 and 424 may be spaced apart and each adjacent to the translucent container 412 when the clamping members 402 and 404 are disposed in the analysis position.

While the present description refers to clamping members 402 and 404 rotatable between a container accepting position and an analysis position, the clamping members may follow translation(s), rotation(s), any combination thereof, or the like to move between the container receiving position and the analysis position. The clamping members 402 and 404 may have any adequate shape allowing the clamping members to abut the protective casing and move the protective casing from the closed position to the open position while moving from the container receiving position to the analysis position. For example, the clamping members may be substantially semicircular, triangular, or the like.

The laser connected to the optical waveguide inserted into a clamping member and illuminating the fluid sample may be continuously operated. In this case, the clamping members act as a shutter for the laser. As such, when the clamping member is disposed in the container accepting position, the contacting portions face the frame of the sample holder so that the light emitted by the optical waveguide is prevented from propagating outside of the sample holder. In other words, when the clamping members are disposed in their open, container accepting, positions, the slots 430 and 432 are not aligned with the light emitted by the optical waveguide and thus act as a shutters which block the laser light and prevent it from reaching the fluid container. When the clamping members are rotated into their closed, analysis, position, the slots 430 and 432 substantially align in a manner sufficient to permit the light emitted by the optical waveguide to penetrate through at least one of the clamping members and into the fluid sample within the exposed portion of the translucent fluid container, and the scattered light to be subsequently collected through the slot in the other clamping member.

The embodiments of the invention described above are therefore intended to be exemplary only. The scope of the invention is intended to be limited solely by the appended claims.

The invention claimed is:

1. A sampling set for extraction of a fluid sample from a fluid reservoir for optical analysis of the fluid sample, the sampling set comprising:
a sample container defined by a body having a conduit extending therethrough between an inlet end adapted to be connected to the fluid reservoir and an analysis end, the analysis end including a translucent container enclosed within a protective case, wherein
the protective case is movable from a closed position in which the translucent container is protected by the protective case and an open position in which at least a portion of the translucent container is exposed outside of the protective case;
a sample container holder having a sample container receiving seat and first and second movable sample container clamps mounted on opposite sides of the receiving seat, each of said first and second sample container clamps having a protective case engaging portion and a heating/cooling source in thermal connection with at least one of the first and second sample container clamps, the heating/cooling source adapted to transfer heat to or from a fluid sample in the translucent container, wherein
said first and second sample container clamps are movable between a sample container accepting position in which the sample container holder is adapted for receiving the sample container in the sample container receiving seat and an analysis position, wherein
in the sample container accepting position the protective case is in the closed position and in the analysis position the protective case engaging portion of the first and second sample container clamps engage an abutting portion of said protective case and the protective case is in the open position.

2. The sampling set according to claim 1 including an optical path extending through the translucent container when the protective case is in the open position.

3. The sampling set according to claim 2 wherein when the protective case is in the open position the optical path extends through both of the first and second sample container clamps.

4. The sampling set according to claim 3 including a light source optically connected to the optical path in one of the first or second sample container clamps.

5. The sampling set according to claim 4 including a light detector optically connected to the optical path in the opposite of the first or second sample container clamps.

6. The sampling set according to claim 2 wherein the optical path is further defined by each of the first and second sample container clamps defining at least one optical waveguide slot, the optical waveguide slots aligned with the translucent container when the first and second sample container clamps are in the second positions.

7. The sampling set according to claim 6 wherein the first and second sample container clamps each comprise a contacting portion having a groove for receiving the translucent container, the contacting portions abutting one another and the container receiving grooves forming a channel for receiving the translucent container when the first and second sample container clamps are in the second position.

8. The sampling set according to claim 7 wherein the container receiving groove is V-shaped.

9. The sampling set according to claim 1 wherein the sample container further comprises a suction generator fluidly connected to the conduit.

10. The sampling set according to claim 9 in which the suction generator is defined by a bellows in the protective case.

11. The sampling set according to claim 10 in which movement of the protective case from the closed position to the open position causes suction in the conduit and fluid to flow from the fluid reservoir into the translucent container.

12. The sampling set according to claim 1 in which the heating/cooling source comprises a Peltier-type thermoelectric module.

* * * * *